United States Patent
Schwamb, Jr.

(10) Patent No.: US 8,320,995 B2
(45) Date of Patent: Nov. 27, 2012

(54) FIDUCIAL MARKER WITH RINGS

(76) Inventor: John P. Schwamb, Jr., Manchester, NH (US)

( * ) Notice: Subject to any disclaimer, the term of this patent is extended or adjusted under 35 U.S.C. 154(b) by 1133 days.

(21) Appl. No.: 11/779,918

(22) Filed: Jul. 19, 2007

(65) Prior Publication Data

US 2008/0269601 A1 Oct. 30, 2008

Related U.S. Application Data

(60) Provisional application No. 60/914,813, filed on Apr. 30, 2007.

(51) Int. Cl.
*A61B 5/00* (2006.01)

(52) U.S. Cl. ........................................ 600/431

(58) Field of Classification Search ............... 600/416, 600/426, 431; 378/204; 424/423
See application file for complete search history.

(56) References Cited

U.S. PATENT DOCUMENTS

| | | | |
|---|---|---|---|
| 6,371,904 B1 * | 4/2002 | Sirimanne et al. | 600/3 |
| 2002/0087101 A1 * | 7/2002 | Barrick et al. | 600/587 |
| 2003/0028095 A1 * | 2/2003 | Tulley et al. | 600/422 |
| 2005/0020916 A1 * | 1/2005 | MacFarlane et al. | 600/431 |
| 2007/0093726 A1 * | 4/2007 | Leopold et al. | 600/562 |

* cited by examiner

*Primary Examiner* — Jonathan Cwern

(74) *Attorney, Agent, or Firm* — Mirick, O'Connell, Demallie & Lougee, LLP

(57) ABSTRACT

An interstitial marker for the location of one of an organ, tumor and tumor bed within a mammalian body includes a plurality of rings having an inner diameter and a ribbon positioned within the inner diameters of the plurality of rings. The plurality of rings may be of the same material or different materials. The materials are visible under different imaging modalities. The ribbon similarly may be of a material visible under various imaging modalities. Tips are attached to the ribbon to hold the rings in place. Alternatively, one or more of the rings may be attached to the ribbon. A helical coil may also be used in connection with a central ribbon for improved imaging. A plurality of coils, of the same material or different materials, may be positioned on a ribbon for a marker.

17 Claims, 3 Drawing Sheets

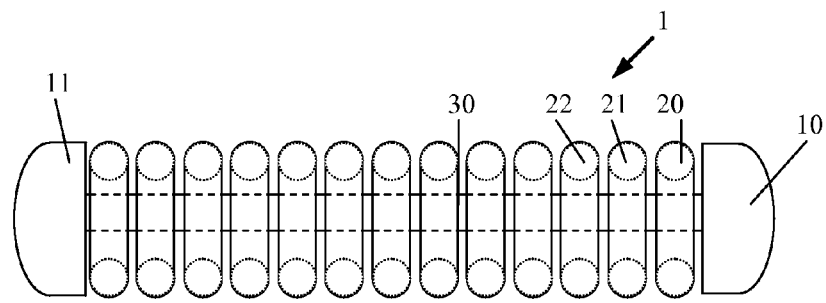
FIG. 1
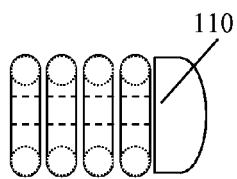
FIG. 2A
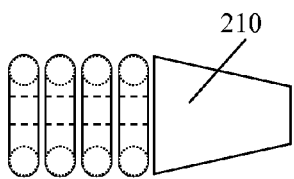
FIG. 2B
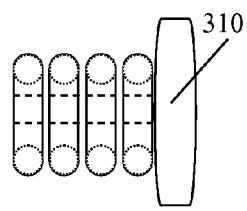
FIG. 2C
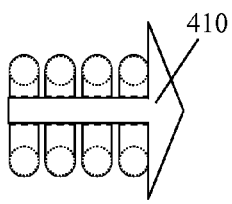
FIG. 2D
FIG. 3A
FIG. 3B
FIG. 3C
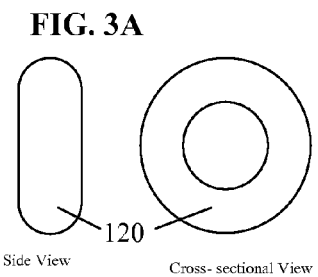
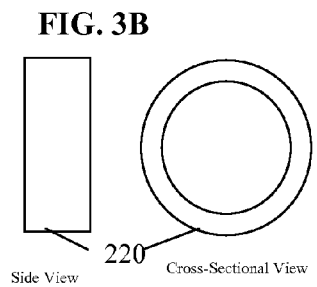
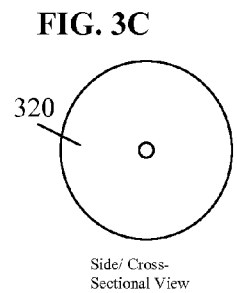
FIG. 3D
FIG. 3E
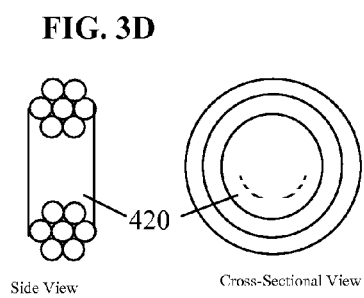
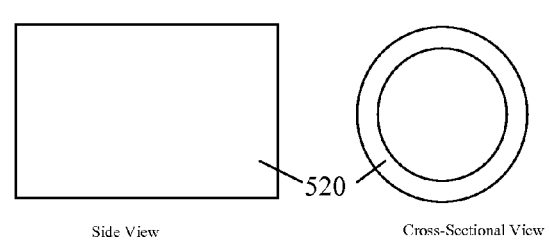

FIDUCIAL MARKER WITH RINGS

CROSS-REFERENCE TO RELATED APPLICATIONS

This application claims priority to U.S. Provisional Application No. 60/914,813, filed Apr. 30, 2007.

BACKGROUND OF THE INVENTION

1. Field of the Invention

The present invention relates to an interstitial marker for localization of organs, tumors and tumor beds using various imaging modalities. More particularly, it relates to an interstitial marker formed of a plurality off concentric rings joined on a inner ribbon.

2. Discussion of Related Art

Interstitial markers have long been known to the medical world. They have been used to prepare patients undergoing radiation treatment whereas such treatments are usually split into daily doses or fractions. The markers help the radiation treat the same area each time treatment is performed on a given patient's tumor. Additional uses of interstitial markers are in the tracking of the location of a suspected tumor during biopsy and the tracking of the volume or the changing volume of a tumor over time either increasing or decreasing in size to gage treatment effectiveness.

Historically markers have been produced of metal "seeds" pre-shaped in the form of a grain of rice or a sphere. Other markers have been in the design of a pre-formed metal coil. Both types of design can have limitations. The solid "seed" type designs have been known to move or migrate from the intended tissue. Movement and/or migration of the marker eliminates the ability to target the intended tissue. The coil design is more stable in tissue and can be viewed under more imaging modalities but it is subject to both compression and elongation, both of which can negate the usefulness of the marker.

In some instances, flexibility of an interstitial marker can be useful for monitoring organs and tumors. For example, a flexible marker may change position and shape as a tumor grows or shrinks. In order to achieve sufficient flexibility, the dimensions of the marker are small. A small marker does not appear as well in the various imaging modalities. Some existing markers have sought to improve the visibility of the marker while maintaining its flexibility though creation of a helical coil from a fine wire. However, such markers can still be difficult to locate due to the small size of the wire. The cross sectional density of the material makes a maker more or less visible than other under most common imaging modalities. Even when using a very dense material, a very small coil will not have a thick enough cross section of material to be visible when imaged. A coil produced from fine wire has an almost smooth texture. This smoothness results in an increase chance of movement in the tissue as well as a surface that is less visible under certain imaging modalities.

Interstitial markers are used to mark locations for visualization under different types of imaging modalities. Materials used to form a marker appear differently under different imaging modalities. Therefore, a marker from a single material may work well with some modalities and not as well for others.

SUMMARY OF THE INVENTION

The present invention provides an interstitial marker which is formed of a plurality of rings. According to one aspect of the invention, the rings are strung along a ribbon. According to another aspect of the invention, tips are connected to each end of the ribbon to hold the rings in place. According to another aspect of the invention, the tips are shaped for visibility under an imaging modality.

According to another aspect of the invention, the rings are formed of a material visible under an imaging modality. According to another aspect of the invention, rings within an interstitial marker are formed of different materials which are visible under different imaging modalities. According to another aspect of the invention, rings have different cross sections and/or different sizes. According to another aspect of the invention, the rings and ribbon are arranged to allow different shapes and movements of the interstitial marker.

According to another aspect of the invention, the interstitial marker includes at least one helical coil and a ribbon positioned within the coil. According to another aspect of the invention, the interstitial marker includes a plurality of coils.

BRIEF DESCRIPTION OF THE DRAWINGS

FIG. 1 is a side view of an interstitial marker according to an embodiment of the present invention.

FIGS. 2A-2D are side views of tips on an interstitial marker according to embodiments of the present invention.

FIGS. 3A-3E are side and cross-sectional views of rings for an interstitial marker according to embodiments of the present invention.

DETAILED DESCRIPTION

Figure 4:
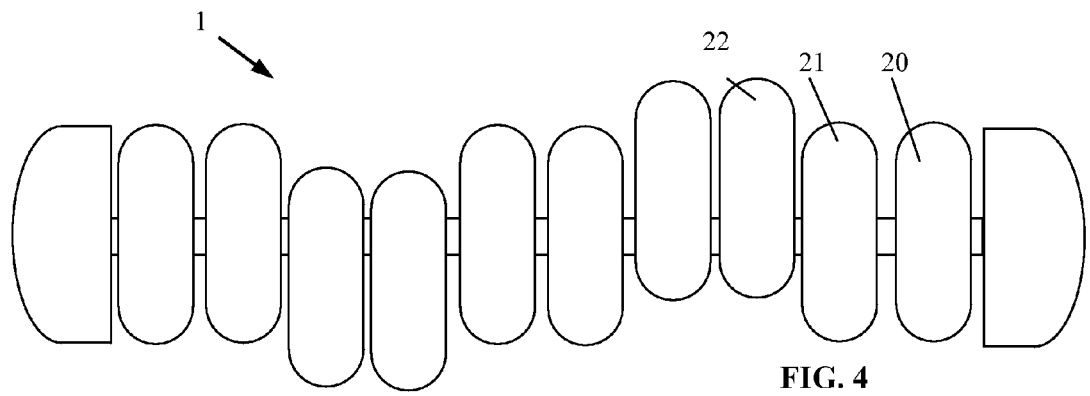
FIG. 4 is a side view of an interstitial marker according to a second embodiment of the present invention.

A fiducial or interstitial marker 1 according to an embodiment of the invention is formed of a plurality of rings 20, 21, 22, as illustrated in FIG. 1. The rings 20, 21, 22 may be of different sizes and shapes, as discussed below. Each of the rings 20, 21, 22 includes a central hole. The central hole may be axially centered, as illustrated in FIG. 1, or may be off-set at any position in the ring. According to embodiments of the invention, the rings may have outside diameters ranging from 0.25 mm to 2.00 mm. The wall thicknesses of the rings may range from 0.025 mm to 0.95 mm. The ring wire widths (when seen from the side as illustrated in FIG. 1) may range from 0.001 cm to 10.0 cm. Typically, markers range from 3.0 mm to 10.0 cm. The widths, number and spacing of the rings are adjusted to obtain a marker of desired length. Although all of the rings in FIG. 1 are illustrated as being of similar size, shape and width. A single marker may include different rings.

The rings may be formed of various materials which are visible under different imaging modalities. Such materials include gold, gold-gallium, platinum, platinum-gold-iridium, platinum-tungsten, platinum-iridium, platinum-nickel, palladium, rhodium, platinum-rhodium, platinum ruthenium, tantalum, 304 stainless steel, 316 stainless steel, 1605, MP35N, Nitinol, and plastic. The size and material of the rings may be selected based upon the primary imaging modality being used.

The rings 20, 21, 22 are held in place by a ribbon 30 which passes through the central holes in the rings. The ribbon 30 prevents the marker from compressing or elongating. The ribbon 30 can be created in different forms such as round wire, flat wire, braided wire or a tubular member. The ribbon may be of any size up to the inner diameters of the rings. According to embodiments of the invention, the diameter of the ribbon ranges from 0.001 mm to 1.00 mm. Preferably, the ribbon 30 is of a material which is visible in an imaging modality, such as the materials set forth above with respect to the rings. It may be of the same material as the rings or a different material. Materials for the rings and ribbon preferably include dense precious metals, such as gold, platinum, tungsten iridium, rhodium and palladium, because these metals are visible under various imaging modalities. For example, the materials can be radiopaque, visible under ultrasound, visible under diagnostic X-ray, and visible under therapeutic X-ray. Alloys of such metals may also be used. Some or all of the components of the marker may use materials which are not as visible but have other beneficial properties. For example, stainless steel and Nitinol may be used since they have specific mechanical properties, such as strength and resistance to deformation, which may be useful in a marker. The rings can be configured from biocompatible material for implantation.

Tips 10, 11 are connected to each end of the ribbon 30. The tips 10, 11 may be of various shapes as illustrated in FIGS. 2A-2D. For example, the tips can be configured as having a D-shaped cross-section 110 (FIG. 2A), a trapezoid shaped cross-section 210 (FIG. 2B), a disk-shaped cross-section 310 (FIG. 2C), or a triangular-shaped cross-section 410 (FIG. 2D). The same shape may be used for both tips 10, 11 or different shapes may be used on each end of the ribbon 30. The shape of the tips 10, 11 may differentiate the ends for use in imaging the marker. The shapes may also be used to assist with anchoring the marker in place. The tips 10, 11 may be of the same or different materials as the ribbon, rings or each other.

The rings 20, 21, 22 of the fiducial marker may exist in different forms. As illustrated in FIG. 1, the rings may be round circular rings. FIGS. 3A-3E illustrate other embodiments for the rings. FIG. 3A illustrates a round ring 120 as in FIG. 1. FIG. 3B illustrates a flat ring 220 having a larger central hole. FIG. 3C illustrates a spherical ring 320 with a small central hole. Rings may be formed as a solid or in a braided form 420 as illustrated in FIG. 3D. Rings many have different widths. FIG. 3E illustrates a tubular ring 520 similar to the flat ring 220 of FIG. 3B, but having a greater length. FIGS. 3A-3E are merely illustrative of possible configurations for the rings. Any size and shape rings may be used. The selected form for the rings may depend upon the intended imaging modalities. The shapes and configurations of rings may have different appearances under different imaging modalities.

Combinations of different diameter or design sections may be used to produce different visualization and performance results. The ribbon 30 can be independent of the rings allowing free movement along the length. The ribbon can also be joined to some or all of the rings creating a spine for the rings. When the ribbon is joined to the rings, a spine forces all of the sections connected to it to be in the same plane. This is advantageous if one desires to have sections that can 'float' independently of the rest of the sections. The floating sections provide additional anchoring power to the marker and minimize the tendency of the coil to move in tissue. Alternatively, the ribbon may be connected to the rings in an offset pattern, as illustrated in FIG. 4. The rings may be connected to the ribbon out of phase. Alternatively, the rings may float on the ribbon so that they may be out of phase. Allowing or attaching the rings out of phase provides for enhanced stability in tissue. The tips 10, 11 can be eliminated from the marker if the ribbon is attached to the outermost rings.

Figure 5:
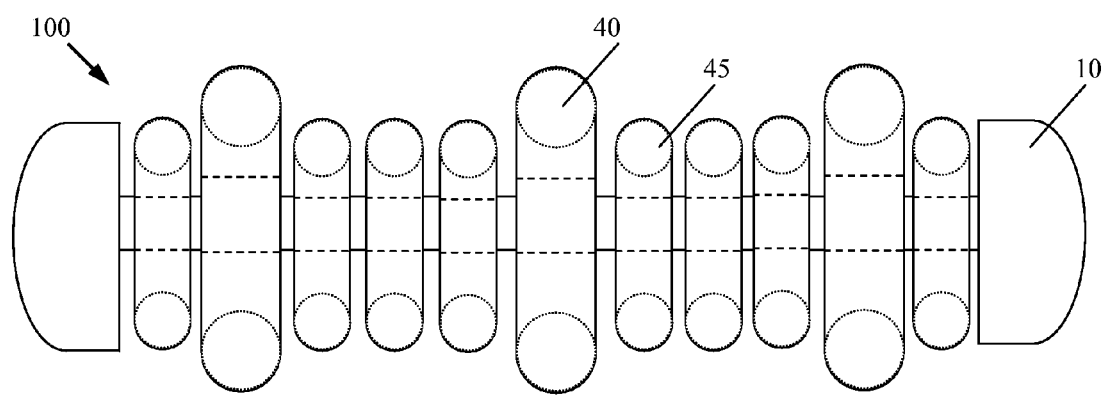
FIG. 5 is a side view of an interstitial marker according to a third embodiment of the present invention.

FIG. 5 illustrates another embodiment of the fiducial marker 100 of the present invention. In this embodiment, a first set of rings 40 are of one size or shape. A second set of rings 45 of are of a different size or shape. The use of different sizes or shapes of rings within a single marker provides for enhanced stability in tissue. Of course, the ordering of the different size or shape rings may be varied. Also, more than two sizes and/or shapes of rings could be used in a marker.

Figure 6:
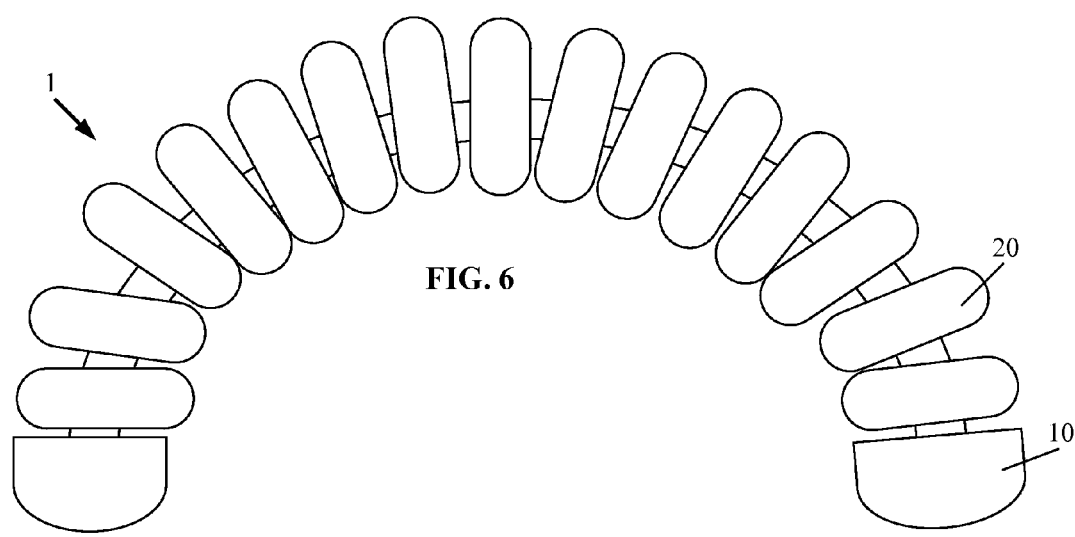
FIG. 6 is a side view of an interstitial marker according to an embodiment of the present invention.

The use of the rings with a ribbon allows the marker to be flexible. Depending upon the spacing between the rings and the length of the ribbons, the marker may have significant flexibility, as illustrated in FIG. 6.

Figure 7:
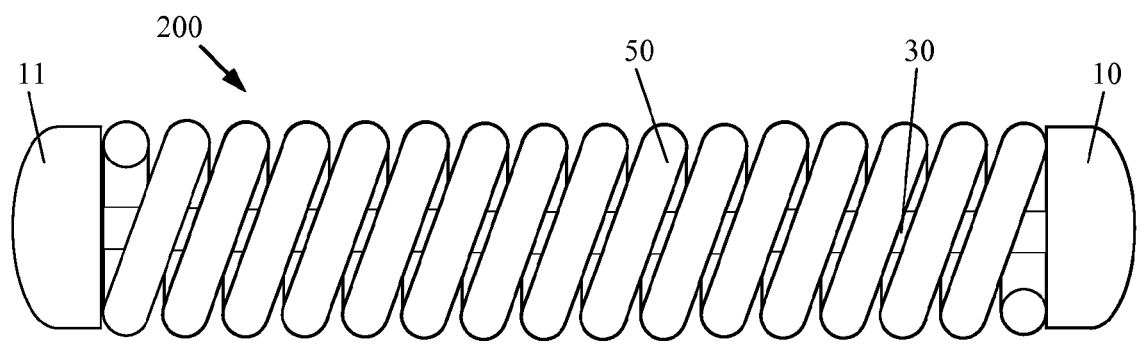
FIG. 7 is a side view of an interstitial marker according to a fourth embodiment of the present invention.

According to another embodiment of the present invention, as illustrated in FIG. 7, a fiducial marker 200 includes at least one helical coil 50. In order to improve the visibility of the marker, a ribbon 30 is positioned within the coil 50. The turns of the coil 50 function in the same manner as the rings of the prior embodiments. Tips 10, 11 are connected to either end of the ribbon 30 to hold the coil in place. As with the other embodiments, the ribbon can float within the coil or can be attached to turns of the coil. By attaching the ends of the ribbon 30 to the outer turns of the coil 50, the tips 10, 11 can be eliminated. In other embodiments of the invention, multiple coils 50 are used in a single marker.

Having disclosed at least one embodiment of the present invention, various adaptations, modifications, additions, and improvements will be readily apparent to those of ordinary skill in the art. Such adaptations, modifications, additions and improvements are considered part of the invention which is only limited by the several claims attached hereto.

The invention claimed is:

1. An interstitial marker for the location of one of an organ, tumor and tumor bed within a mammalian body, the marker comprising:
    a plurality of adjacent rings, each ring of the plurality of adjacent rings being configured as a closed band defining a circular curve and having an inner diameter;
    a ribbon positioned within the inner diameters of the adjacent rings, each ring of the plurality of adjacent rings and the ribbon comprising a material visible under a common imaging modality; and
    at least one tip connected to an end of the ribbon;
    wherein the at least one tip is formed of a material visible under at least one imaging modality; and
    wherein the at least one tip includes:
    a first tip having a D-shaped cross-section, the first tip secured to a first end of the ribbon,
    a second tip having a D-shaped cross-section the second tip secured to a second end of the ribbon, the second end opposing the first end,
    the first tip and the second tip each having an outer diameter that is greater than the inner diameter of each ring of the plurality of adjacent rings, and
    the first tip and the second tip being configured to capture the plurality of adjacent rings along the ribbon there between, each ring of the plurality of adjacent rings being configured to translate along a longitudinal axis of the ribbon between the first tip and the second tip.

2. The interstitial marker according to claim 1 wherein each of the plurality of rings and the ribbon is comprised of a dense, precious metal.

3. The interstitial marker according to claim 1 wherein the plurality of adjacent rings include a first set of rings having a first set of dimensions and a second set of rings having a second set of dimensions.

4. The interstitial marker according to claim 1 wherein each of the plurality of rings is movable with respect to the ribbon.

5. The interstitial marker according to claim 1 wherein the ribbon is attached to at least one of the rings so that the at least one ring does not move with respect to the ribbon.

6. The interstitial marker according to claim 1 wherein at least one component of the marker, from among the ribbon and the plurality of rings, comprises a radiopaque material.

7. The interstitial marker according to claim 1 wherein at least one component of the marker, from among the ribbon and the plurality of rings, comprises a material visible under ultrasound imaging.

8. The interstitial marker according to claim 1 wherein at least one component of the marker, from among the ribbon and the plurality of rings, comprises a material visible under diagnostic x-ray.

9. The interstitial marker according to claim 1 wherein at least one component of the marker, from among the ribbon and the plurality of rings, comprises a material visible under therapeutic x-ray.

10. The interstitial marker according to claim 1 wherein the ribbon and the rings comprise biocompatible materials for implantation.

11. The interstitial marker according to claim 1 wherein:
a first one of the plurality of rings is of a first material; and
a second one of the plurality of rings is of a second material.

12. The interstitial marker of claim 1, wherein the plurality of adjacent rings are configured to secure the interstitial marker at a tissue location.

13. The interstitial marker of claim 12, wherein the plurality of adjacent rings, the first tip, and the second tip are configured to anchor the interstitial marker at the tissue location.

14. An interstitial marker for the location of one of an organ, tumor and tumor bed within a mammalian body, the marker comprising:
a helical coil having a first free end, a second free end opposing the first free end, and a set of coil elements disposed between the first free end and the second free end;
a ribbon positioned within the helical coil, the helical coil and the ribbon comprising a material visible under a common imaging modality;
a first tip disposed at a first end of the ribbon and a second tip disposed at a second end of the ribbon, the second end of the ribbon opposing the first end of the ribbon; and
the first free end, the second free end, and the set of coil elements of the helical coil being configured to translate along a longitudinal axis of the ribbon between the first tip and the second tip;
wherein the first tip and the second tip are each formed of a material visible under at least one imaging modality; and
wherein:
the first tip comprises a D-shaped cross-section, the first tip secured to the first end of the ribbon,
the second tip comprises a D-shaped cross-section the second tip secured to the second end of the ribbon,
the first tip and the second tip each having an outer diameter that is greater than an inner diameter of each coil element of the set of coil elements, and
the first tip and the second tip being configured to capture the set of coil elements along the ribbon there between.

15. The interstitial marker of claim 14, wherein the set of coil elements, the first tip, and the second tip are configured to anchor the interstitial marker at a tissue location.

16. An interstitial marker for the location of one of an organ, tumor and tumor bed within a mammalian body, the marker comprising:
a plurality of adjacent rings, each ring of the plurality of adjacent rings being configured as a closed band defining a circular curve and having an inner diameter;
a ribbon positioned within the inner diameters of the adjacent rings, each ring of the plurality of adjacent rings and the ribbon comprising a material visible under a common imaging modality; and
at least one tip connected to an end of the ribbon;
wherein the at least one tip is formed of a material visible under the common imaging modality; and
wherein the at least one tip includes:
a first tip secured to a first end of the ribbon,
a second tip secured to a second end of the ribbon, the second end opposing the first end,
the first tip and the second tip each having an outer diameter that is greater than the inner diameter of each ring of the plurality of adjacent rings, and
the first tip and the second tip being configured to capture the plurality of adjacent rings along the ribbon there between, each ring of the plurality of adjacent rings being configured to translate along a longitudinal axis of the ribbon between the first tip and the second tip.

17. An interstitial marker for the location of one of an organ, tumor and tumor bed within a mammalian body, the marker comprising:
a helical coil having a first free end, a second free end opposing the first free end, and a set of coil elements disposed between the first free end and the second free end;
a ribbon positioned within the helical coil, the helical coil and the ribbon comprising a material visible under a common imaging modality;
a first tip disposed at a first end of the ribbon and a second tip disposed at a second end of the ribbon, the second end of the ribbon opposing the first end of the ribbon; and
the first free end, the second free end, and the set of coil elements of the helical coil being configured to translate along a longitudinal axis of the ribbon between the first tip and the second tip;
the first tip and the second tip each being formed of a material visible under the common imaging modality;
the first tip secured to the first end of the ribbon;
the second tip secured to the second end of the ribbon;
the first tip and the second tip each having an outer diameter that is greater than an inner diameter of each coil element of the set of coil elements, and
the first tip and the second tip being configured to capture the set of coil elements along the ribbon there between.

* * * * *